United States Patent
Kondo

(10) Patent No.: US 7,143,632 B2
(45) Date of Patent: Dec. 5, 2006

(54) GAS DETECTING METHOD, AND GAS DETECTING DEVICE

(75) Inventor: Yoshinari Kondo, Tsukuba (JP)

(73) Assignee: High Energy Accelerator Research Organization, Tsukuba (JP)

( * ) Notice: Subject to any disclaimer, the term of this patent is extended or adjusted under 35 U.S.C. 154(b) by 15 days.

(21) Appl. No.: 10/890,124

(22) Filed: Jul. 14, 2004

(65) Prior Publication Data

US 2005/0034536 A1   Feb. 17, 2005

(30) Foreign Application Priority Data

Jul. 23, 2003   (JP) ............... 2003-200473

(51) Int. Cl.
*G01F 1/66*   (2006.01)

(52) U.S. Cl. ............ 73/24.01; 73/24.06; 73/597; 73/602

(58) Field of Classification Search ........... 73/24.01, 73/24.06, 592, 597, 602, 861.27
See application file for complete search history.

(56) References Cited

U.S. PATENT DOCUMENTS

| | | | | |
|---|---|---|---|---|
| 3,429,177 A | * | 2/1969 | Krupnick et al. | 73/24.01 |
| 5,537,854 A | * | 7/1996 | Phillips et al. | 73/24.01 |
| 5,581,014 A | * | 12/1996 | Douglas | 73/24.01 |
| 6,202,468 B1 | * | 3/2001 | Dempster et al. | 73/23.2 |
| 6,279,378 B1 | * | 8/2001 | Sheen et al. | 73/24.01 |
| 6,820,462 B1 | * | 11/2004 | Cardelius | 73/24.01 |
| 6,823,715 B1 | * | 11/2004 | Kobayakawa et al. | 73/24.06 |

FOREIGN PATENT DOCUMENTS

| | | |
|---|---|---|
| JP | U 5-84847 | 11/1993 |
| JP | A 8-94590 | 4/1996 |
| JP | A 9-79934 | 3/1997 |
| JP | A 10-306312 | 11/1998 |
| JP | A 2000-249435 | 9/2000 |
| JP | A 2001-56320 | 2/2001 |

* cited by examiner

*Primary Examiner*—Daniel S. Larkin
(74) *Attorney, Agent, or Firm*—Oliff & Berridge, PLC

(57) ABSTRACT

An electronic signal relating to a sonic wave when an intended gas does not exist in air is synchronized and locked in a feedback circuit constituting a phase-locked loop (PLL). Then, an electronic signal relating to another sonic wave when the intended gas exist in the air is input into the feedback circuit to release the synchronization (lock) of the feedback circuit to measure as a given electronic signal the difference in phase of the sonic wave in the air between with and without the intended gas to be detected. The intended gas can be detected as the electronic signal due to the difference in phase of the sonic wave.

13 Claims, 2 Drawing Sheets

GAS DETECTING METHOD, AND GAS DETECTING DEVICE

BACKGROUND OF THE INVENTION

1. Field of the Invention

This invention relates to a gas detecting method and a gas detecting device which are preferably usable for detecting gas leaks in a technical field requiring long times and continuous gas detection, such as mining and manufacturing fields, petrochemical fields or high pressure gas producing facilities.

2. Description of the Prior Art

As an atmosphere gas detecting method, as of now, is established a chemical reaction type gas detecting method using a galvanic battery and a constant potential electrolysis and a gas thermal conduction difference type gas detecting method. The conventional gas detecting method enables an intended gas to be detected at high sensitivity and high precision.

With the conventional gas detecting method, however, since chemical reaction or thermal conduction is employed, the sensor to be installed into the gas detecting device is always consumed. Therefore, it is always required in the conventional gas detecting device that the installed sensor is exchanged regularly, so that the conventional gas detecting device is not suitable for long duration and continuous use. With the gas detecting method using the thermal conduction difference, it is required that the zero adjustment is performed for the gas detecting device appropriately before the use and/or during the use, so that the gas detecting method can not be employed stably.

SUMMERY OF THE INVENTION

It is an object of the present invention to detect an intended gas easily for a long time without frequent zero adjustment.

In order to achieve the above object, this invention relates to a gas detecting method comprising the steps of:
  emitting a sonic wave in an atmosphere without an intended gas to be detected to measure a sonic wave velocity of the sonic wave as a first sonic wave velocity;
  emitting the sonic wave in another atmosphere with the intended gas to be detected to measure another sonic wave velocity of the sonic wave as a second sonic wave velocity; and
  obtaining a difference between the first sonic wave velocity and the second sonic wave velocity to detect the intended gas.

According to the gas detecting method of the present invention, the difference in sonic wave velocity between the sonic wave in the space where the intended gas does not exist, such as atmosphere, and the sonic wave in the space where the intended gas exists is employed, and detected so that the intended gas is detected. Without the sensor exchange as in the conventional gas detecting method using the chemical reaction or the thermal conduction, therefore, the intended gas can be detected stably for a long time.

Moreover, when the sonic wave source is made of a stable sonic wave source, such as a quartz crystal oscillator, the frequent zero adjustment is not required for the gas detecting device only if the initial zero adjustment is done. Therefore, the gas detecting operation can be simplified.

In a preferred embodiment of the present invention, the difference between the first sonic wave velocity and the second sonic wave velocity is obtained from a given feedback circuit. In this case, since the first sonic wave velocity and the second sonic wave velocity are converted into respective input electronic signals, such as pulse train electronic signals, and noises are eliminated from the electronic signals by various circuit operation, the difference between the first sonic wave velocity and the second sonic wave velocity can be obtained easily and high precisely. Moreover, the difference between the first sonic wave velocity and the second sonic wave velocity can be calculated constantly while the intended gas to be detected exists. Therefore, the remanence of the intended gas can be detected.

In another preferred embodiment of the present invention, the feedback circuit constitutes a phase-locked loop (PLL). In this case, in the feedback circuit, a given electronic signal can be applied to the first input electronic signal relating to the first sonic wave velocity where the intended gas to be detected does not exist so that the phase of the first input electronic signal is synchronized (locked) with the phase of the applied electronic signal. When the intended gas exists, the second input electronic signal relating to the second sonic wave velocity is introduced into the feedback circuit and the synchronization (lock) is released in the feedback circuit. Therefore, if the difference electronic signal relating to the thus obtained phase difference is detected, the intended gas can be detected easily.

With the above-mentioned gas detecting method, for example, an alarm set station can be driven with the detected difference electronic signal to announce the existence of the intended gas to an operator with sound or buzzer.

A gas detecting device according to the present invention is employed in order to carry out the above-mentioned gas detecting method, and comprises:
  a sonic wave source to generate a given sonic wave;
  a sonic wave emitter to emit the sonic wave into air,
  a sonic wave receiver to receive the sonic wave; and
  a measuring means to compare a first sonic wave velocity without an intended gas to be detected in the air with a second sonic wave velocity with the intended gas to be detected in the air to calculate a difference between the first sonic wave velocity and the second sonic wave velocity.

In the gas detecting device of the present invention, it is desired that the measuring means includes a given feedback circuit, and the feedback circuit constitutes a PLL on the same reason as the gas detecting method of the present invention.

Other advantages and details of the present invention will be described hereinafter.

BRIEF DESCRIPTION OF THE DRAWINGS

For better understanding of the present invention, reference is made to the attached drawings, wherein.

DESCRIPTION OF THE PREFERRED EMBODIMENTS

Figure 1:
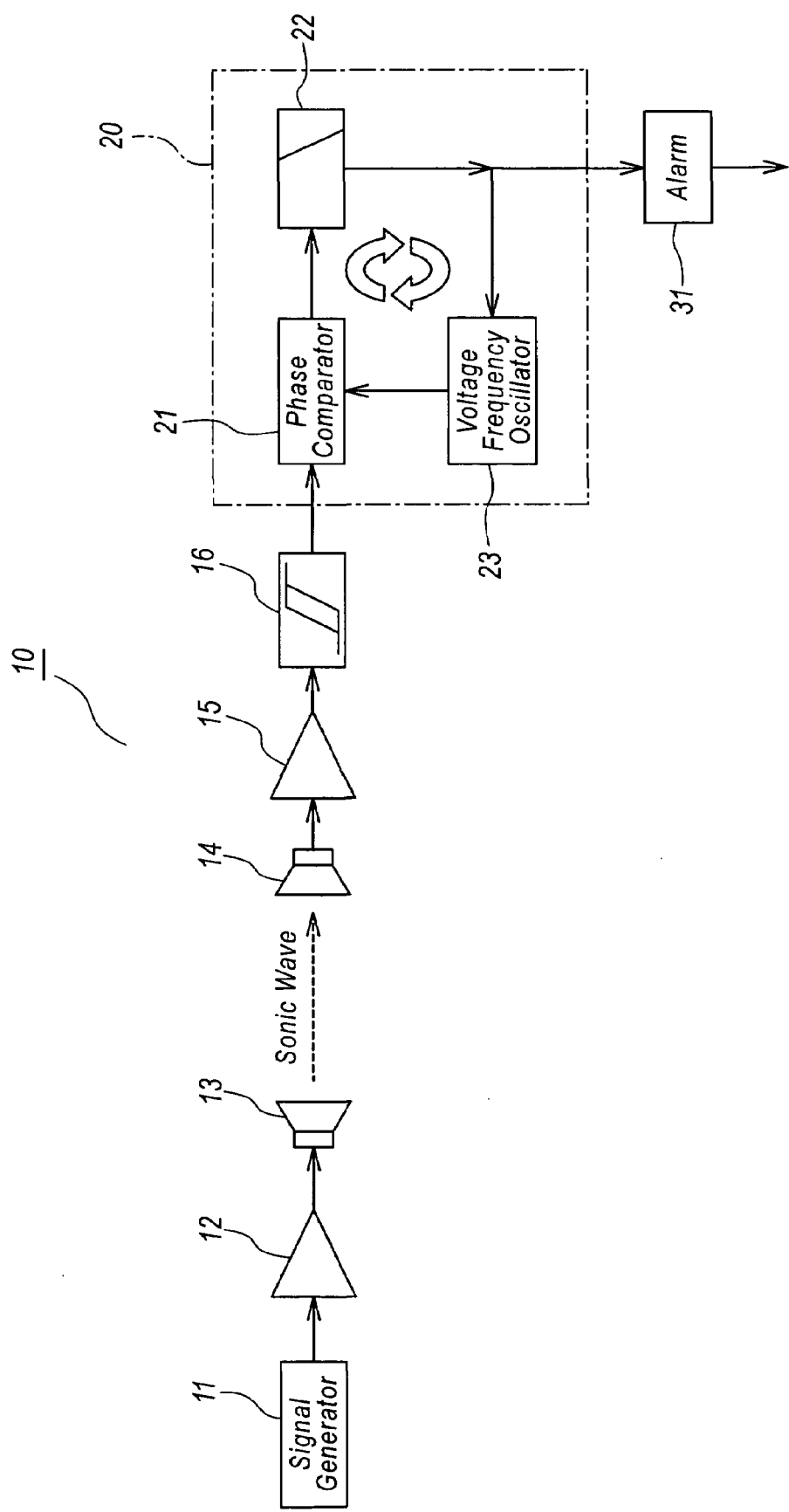
FIG. 1 is a structural view illustrating a gas detecting device according to the present invention.
Figure 2:
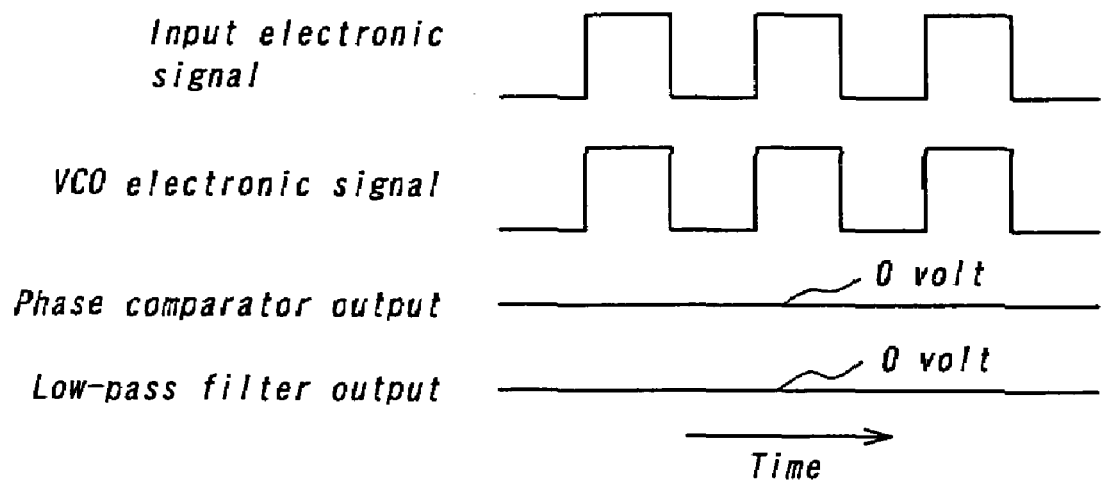
FIG. 2 is an explanatory view for the gas detection using the gas detecting device illustrated in FIG. 1.
Figure 3:
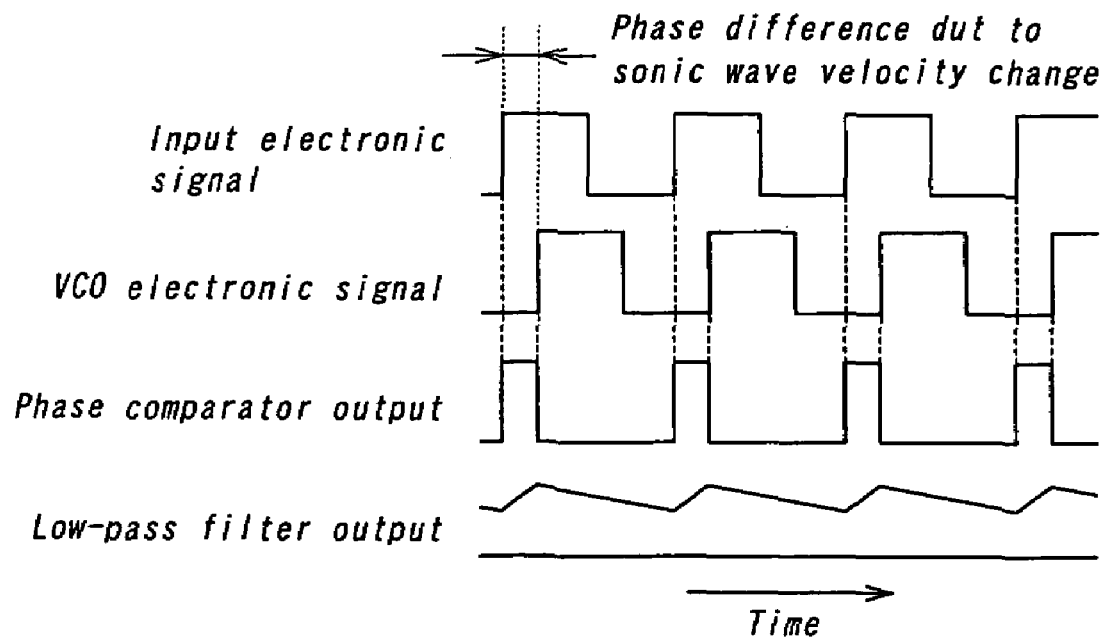
FIG. 3 is another explanatory view for the gas detection using the gas detecting device illustrated in FIG. 1.

This invention will be described in detail with reference to the accompanying drawings. FIG. 1 is a structural view illustrating a gas detecting device according to the present invention, and FIGS. 2–3 are explanatory views for the gas detection using the gas detecting device illustrated in FIG. 1. The gas detecting device 10 illustrated in FIG. 1 includes a standard signal generator 11 as a sonic wave source made of a quartz crystal oscillator or the like, a supersonic speaker 13 as a sonic wave emitter to emit an sonic wave from the generator 11 into air, and a supersonic microphone 14 as a sonic wave receiver to receive the sonic wave emitted into air.

A speaker driving amplifier 12 to drive the speaker 13 and amplify the sonic wave is provided between the standard signal generator 11 and the supersonic speaker 13, and a front amplifier 15 and a wave form shaper 16 are provided in the rear of the supersonic microphone 14.

A feedback circuit 20 constituting PLL is provided in the rear of the wave form shaper 16. The feedback circuit 20 is composed of a phase comparator 21, a low-pass filter 22 and a voltage frequency oscillator 23. An alarm set station 31 is provided in the rear of the feedback circuit 20.

With the gas detecting device 10 illustrated in FIG. 1, an intended gas to be detected is flowed between the supersonic speaker 13 and the supersonic microphone 14.

With the gas detecting device 10 illustrated in FIG. 1, a given electronic signal is oscillated from the standard signal generator 11, amplified at the speaker driving amplifier 12, and emitted as a supersonic wave into air from the supersonic wave speaker 13. The supersonic wave is received at the supersonic microphone 14 and converted into a pulse train electronic signal, which is amplified at the front amplifier 15 and shaped in wave form at the wave form shaper 16. Thereafter, the pulse train electronic signal is input into the feedback circuit 20.

Since the feedback circuit 20 constitutes the PLL, in the feedback circuit 20, as illustrated in FIG. 2, a given pulse train electronic signal (VCO electronic signal) is applied to the pulse train input electronic signal where the intended gas does not exist from the voltage frequency oscillator 23 so that the phase of the input electronic signal is synchronized and locked with the phase of the applied electronic signal. In other words, in the feedback signal, the input electronic signal relating to the non-existence of the intended gas is locked. In this case, a pulse train electronic signal at lock is output from the phase comparator 21, and a standard voltage at lock which is obtained through the integration of the pulse train electronic signal is output from the low-pass filter 22.

In this embodiment, as illustrated in FIG. 2, since the output from the phase comparator 21 is set to zero, the output from the low-pass filter is also set to zero.

In contrast, when the intended gas exists in air, the sonic wave velocity in air of the supersonic wave oscillated from the supersonic speaker 13 becomes different from the sonic wave velocity in air of the supersonic wave when the intended gas does not exist in air, so that as illustrated in FIG. 3, the input electronic signal relating to the supersonic wave at the existence of the intended gas is shifted in phase from the input electronic signal relating to the supersonic wave at the non-existence of the intended gas, that is, the VCO electronic signal synchronized therewith. As a result, at the phase comparator 21, a given electronic signal is generated in dependence upon the difference in phase between the input electronic signal and the VCO electronic signal to be output via the low-pass filter 22.

In this way, the thus obtained difference electronic signal is input into the alarm set station 31 to announce the existence of the intended gas to an operator with sound or buzzer.

The difference in phase between the input electronic signal and the VCO electronic signal is always detected using the feedback mechanism of the feedback circuit 20 until the different in phase is eliminated and the input electronic signal is synchronized and locked again with the VCO electronic signal. In other words, the input electronic signal is automatically compared with the VCO electronic signal until the intended gas to be detected is eliminated, and when the difference in phase between the input electronic signal and the VCO electronic signal is created due to the existence of the intended gas to be detected, the difference electronic signal is output to announce the existence of the intended gas to the operator via the alarm set station 31. Therefore, the remanence of the intended gas can be detected.

Although the present invention was described in detail with reference to the above examples, this invention is not limited to the above disclosure and every kind of variation and modification may be made without departing from the scope of the present invention.

In the above embodiment, the supersonic microphone 14 is provided so as to be opposite to the supersonic speaker 13, and the intended gas is flowed between the supersonic speaker 13 and the supersonic microphone 14, but only if the supersonic wave from the supersonic speaker 13 is introduced into the supersonic microphone 14, the arrangement of the supersonic speaker 13 and the supersonic microphone 14 is not restricted. For example, if the supersonic wave from the supersonic speaker 13 is reflected at a wall (not shown) and introduced into the supersonic microphone 14, the supersonic speaker 13 and the supersonic microphone 14 can be provided back to back. In this case, the intended gas to be detected is flowed in a given space where the supersonic wave is propagated.

In the above embodiment, the supersonic speaker 13 and the supersonic microphone 14 are provided to detect the intended gas using the supersonic wave, but another sonic wave, e.g., a sonic wave within audiofrequency range may be employed in accordance with the sort of the intended gas.

In the above embodiment, the PLL feedback circuit is employed, but instead, another electric circuit to measure the difference in sonic wave velocity of the sonic waves with and without the intended gas to be detected may be employed. In addition, without the electric circuits, the difference in sonic wave velocity can be directly measured.

As mentioned above, according to the present invention can be provided a gas detecting method and a gas detecting device whereby an intended gas can be detected easily and stably for a long time without frequent zero adjustment.

What is claimed is:

1. A gas detecting method comprising:
   emitting a sonic wave in an atmosphere without an intended gas to be detected to measure a sonic wave velocity of said sonic wave as a first sonic wave velocity;
   emitting said sonic wave in another atmosphere with said intended gas to be detected to measure another sonic wave velocity of said sonic wave as a second sonic wave velocity; and
   obtaining a difference between said first sonic wave velocity and said second sonic wave velocity to detect said intended gas,
   wherein said first sonic wave velocity and said second sonic wave velocity are measured as respective electronic signals and said electronic signal is a pulse train electronic signal.

2. The gas detecting method as defined in claim 1, wherein said difference between said first sonic wave velocity and said second sonic wave velocity is obtained in a given feedback circuit.

3. The gas detecting method as defined in claim 2, wherein said feedback circuit constitutes a phase-locked loop (PLL).

4. The gas detecting method as defined in claim 3, wherein with said PLL, a first input electronic signal relating to said first sonic wave velocity is locked through synchronization in phase.

5. The gas detecting method as defined in claim 4, wherein with said PLL, said difference between said first sonic wave velocity and said second wave velocity is obtained as a difference electronic signal in dependence upon a difference in phase between a second input electronic signal relating to said second sonic wave velocity and said first input electronic signal relating to said first sonic wave velocity.

6. The gas detecting method as defined in claim 5, wherein with said feedback circuit, a phase of said first input electronic signal relating to said first sonic wave velocity is compared with a phase of said second input electronic signal relating to said second sonic wave velocity until said phase of first input electronic signal is matched to said phase of said second input electronic signal.

7. The gas detecting method as defined in claim 5, wherein said difference electronic signal is output as a detection signal of said intended gas to be detected.

8. A gas detecting device comprising:
   a sonic wave source to generate a given sonic wave;
   a sonic wave emitter to emit said sonic wave into air;
   a sonic wave receiver to receive said sonic wave; and
   a measuring means to compare a first sonic wave velocity without an intended gas to be detected in said air, said first sonic wave being measured, with a second sonic wave velocity with said intended gas to be detected in said air, said second sonic wave being measured, to calculate a difference between said first sonic wave velocity and said second sonic wave velocity,
   wherein said measuring means includes a feedback circuit constituting a phase-locked loop (PLL).

9. The gas detecting device as defined in claim 8, further comprising an outputting means to output, as a detection signal relating to said intended gas to be detected, a difference electronic signal in dependence upon a difference in phase between a first input electronic signal relating to said first sonic wave velocity and a second input electronic signal relating to said second sonic wave velocity.

10. The gas detecting device as defined in claim 9, wherein said outputting means is an alarm set station.

11. The gas detecting device as defined in claim 8, wherein said sonic wave source is a quartz crystal oscillator.

12. The gas detecting device as defined in claim 8, wherein said sonic wave emitter is a supersonic wave speaker.

13. The gas detecting device as defined in claim 8, wherein said sonic wave receiver is a supersonic wave microphone.

* * * * *